US010000580B2

(12) United States Patent
Kasat et al.

(10) Patent No.: US 10,000,580 B2
(45) Date of Patent: *Jun. 19, 2018

(54) PREPARATION OF POLY ALPHA-1,3-GLUCAN ESTERS AND FILMS THEREFROM

(71) Applicant: E I DU PONT DE NEMOURS AND COMPANY, Wilmington, DE (US)

(72) Inventors: Rahul B Kasat, Wilmington, DE (US); Jayme L Paullin, Claymont, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 128 days.

This patent is subject to a terminal disclaimer.

(21) Appl. No.: 15/058,406

(22) Filed: Mar. 2, 2016

(65) Prior Publication Data

US 2016/0251453 A1 Sep. 1, 2016

Related U.S. Application Data

(63) Continuation of application No. 14/136,226, filed on Dec. 20, 2013, now Pat. No. 9,278,988.

(60) Provisional application No. 61/746,335, filed on Dec. 27, 2012, provisional application No. 61/746,328, filed on Dec. 27, 2012, provisional application No. 61/746,338, filed on Dec. 27, 2012.

(51) Int. Cl.

| | |
|---|---|
| ***C08B 37/00*** | (2006.01) |
| ***C07H 13/04*** | (2006.01) |
| ***C08J 5/18*** | (2006.01) |
| ***C08L 5/00*** | (2006.01) |

(52) U.S. Cl.

CPC ......... *C08B 37/0009* (2013.01); *C07H 13/04* (2013.01); *C08J 5/18* (2013.01); *C08L 5/00* (2013.01); *C08J 2305/00* (2013.01)

(58) Field of Classification Search

None

See application file for complete search history.

(56) References Cited

U.S. PATENT DOCUMENTS

| | | | | |
|---|---|---|---|---|
| 4,501,886 | A * | 2/1985 | O'Brien | D01F 2/28 536/57 |
| 7,000,000 | B1 * | 2/2006 | O'Brien | C12P 19/08 536/123.12 |
| 9,278,988 | B2 * | 3/2016 | Kasat | C07H 13/04 |
| 9,403,917 | B2 * | 8/2016 | Kasat | C08B 37/0009 |
| 2013/0244287 | A1 | 9/2013 | O'Brien et al. | |
| 2013/0244288 | A1 | 9/2013 | O'Brien et al. | |

FOREIGN PATENT DOCUMENTS

| | | |
|---|---|---|
| CN | 1283633 A | 2/2001 |

OTHER PUBLICATIONS

Cerqueira et al., "Optimization of Sugarcane Bagasse Cellulose Acetylation" Carbohydrate Polymers (2007) vol. 69 pp. 579-582.*

Machine Translation, CN1283633, Carboxynethylated Derivative of Ganoderic Alpha-(1,3)D-Glucosan and its Usage and Preparing Process, Wuhan University, Feb. 14, 2001.

Cantarel et al., The Carbohydrate-Active Enzymes Database (CAZY): An Expert Resource for Glycogenomics, Nucleic Acids Research (2009), vol. 37, Database Issue, pp. D233-D238.

Kiho et al., (1-->3)-α-D-Glucan From an Alkaline Extract of Agrocybe Cylindracea, and Antitumor Activity of Its O-(Carboxy-Methyl)ated Derivatives, Carbohydrate Research (1989), vol. 189, pp. 273-279.

Ogawa et al., Crystal Structure of (1-->3)-α-D-Glucan, in Fiber Defraction Methods, ACS Symposium (1990), vol. 47, pp. 353-362.

Ogawa et al., X-ray Diffraction Data for (1-->3)-α-D-Glucan Triacetate, Carbohydrate Poymers (1983), vol. 3, pp. 287-297.

Simpson et al., Four Glucosyltransferases, GTFJ, GTFK, GTFL, and GTFM, From *Streptococcus salivarious* ATCC 25975, Microbiology (1995), vol. 141, pp. 1451-1560.

Yui et al., Molecular and Crystal Structure of (1-->3)-α-D-Glucan Triacetate, Int. J. Biol. Macromol. (1992), vol. 14, pp. 87-96.

Ogawa et al., Confirmation of (1-->3)-α-D-Glucan Tribenzoate, Biosci. Biotech. Biochem., vol. 57, No. 10 (1993), pp. 1663-1665.

* cited by examiner

*Primary Examiner* — Eric Olson

(57) ABSTRACT

Poly alpha-1,3-glucan ester compounds are disclosed herein with a degree of substitution of about 0.05 to about 3.0. Also disclosed are methods of producing poly alpha-1,3-glucan ester compounds and films made therefrom.

24 Claims, No Drawings

PREPARATION OF POLY ALPHA-1,3-GLUCAN ESTERS AND FILMS THEREFROM

This application is a continuation of U.S. application Ser. No. 14/136,226, filed Dec. 20, 2013 (now U.S. Pat. No. 9,278,988), which claims the benefit of U.S. Provisional Application Nos. 61/746,328, 61/746,335 and 61/746,338, each filed Dec. 27, 2012. All these earlier applications are incorporated herein by reference in their entirety.

FIELD OF INVENTION

This invention is in the field of poly alpha-1,3-glucan derivatives. Specifically, this invention pertains to poly alpha-1,3-glucan esters, methods of their preparation, and films made therefrom.

BACKGROUND

Driven by a desire to find new structural polysaccharides using enzymatic syntheses or genetic engineering of microorganisms or plant hosts, researchers have discovered polysaccharides that are biodegradable, and that can be made economically from renewable resource-based feedstocks. One such polysaccharide is poly alpha-1,3-glucan, a glucan polymer characterized by having alpha-1,3-glycosidic linkages. This polymer has been isolated by contacting an aqueous solution of sucrose with a glucosyltransferase enzyme isolated from *Streptococcus salivarius* (Simpson et al., *Microbiology* 141:1451-1460, 1995). Films prepared from poly alpha-1,3-glucan tolerate temperatures up to 150° C. and provide an advantage over polymers obtained from beta-1,4-linked polysaccharides (Ogawa et al., *Fiber Differentiation Methods* 47:353-362, 1980).

U.S. Pat. No. 7,000,000 disclosed the preparation of a polysaccharide fiber comprising hexose units, wherein at least 50% of the hexose units within the polymer were linked via alpha-1,3-glycosidic linkages using an *S. salivarius* gtfJ enzyme. This enzyme utilizes sucrose as a substrate in a polymerization reaction producing poly alpha-1,3-glucan and fructose as end-products (Simpson et al., 1995). The disclosed polymer formed a liquid crystalline solution when it was dissolved above a critical concentration in a solvent or in a mixture comprising a solvent. From this solution, continuous, strong, cotton-like fibers, highly suitable for use in textiles, were spun and used.

Information regarding preparation of various derivatives of poly alpha-1,3-glucan and their application is sparse.

Yui et al. (*Int. J. Biol. Macromol.* 14:87-96, 1992) disclose using poly alpha-1,3-glucan extracted from the fruiting body of the fungus, *Laetiporus silphureus*, to synthesize poly alpha-1,3-glucan triacetate. The structure of this polymer was analyzed by X-ray crystallography.

Ogawa et al. (*Carb. Poly.* 3:287-297, 1983) used three different samples of poly alpha-1,3-glucan to prepare poly alpha-1,3-glucan triacetate. One sample was isolated from a bacterial extracellular polysaccharide, and the other two samples were extracted from fruiting bodies of fungi. The structures of these polymers were analyzed by X-ray crystallography.

Development of new poly alpha-1,3-glucan ester derivatives and methods of preparing such derivatives is desirable given their potential utility in various applications, such as film production.

SUMMARY OF INVENTION

In one embodiment, the invention concerns a composition comprising a poly alpha-1,3-glucan ester compound represented by the structure:

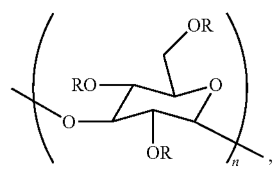

wherein (i) n is at least 6, (ii) each R is independently an H or an acyl group, and (iii) the compound has a degree of substitution of about 0.05 to about 3.0.

In a second embodiment, the acyl group is an acetyl, propionyl, butyryl, pentanoyl, hexanoyl, heptanoyl, or octanoyl group. The compound in this embodiment may contain one type of the acyl group, or two or more types of the acyl group. In a third embodiment, the compound contains one type of the acyl group.

In a fourth embodiment, the acyl group is an acetyl group and the degree of substitution is about 0.05 to about 2.6.

In a fifth embodiment, the compound contains two or more types of the acyl group. For example, the two or more types of the acyl group can be (i) acetyl and propionyl, or (ii) acetyl and butyryl.

In a sixth embodiment, the invention concerns a method for producing a poly alpha-1,3-glucan ester compound. This method comprises contacting poly alpha-1,3-glucan in a reaction that is substantially anhydrous with at least one acid catalyst, at least one acid anhydride, and at least one organic acid. An acyl group derived from the acid anhydride is esterified to the poly alpha-1,3-glucan in this contacting step, thereby producing a poly alpha-1,3-glucan ester compound represented by the structure:

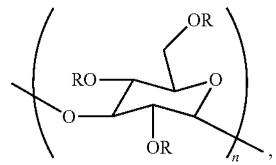

wherein (i) n is at least 6, (ii) each R is independently an H or the acyl group, and (iii) the compound has a degree of substitution of about 0.05 to about 3.0. A poly alpha-1,3-glucan ester produced by this method can optionally be isolated.

In a seventh embodiment, poly alpha-1,3-glucan is acid-exchanged with an organic acid before the contacting step of the method in order to remove water from the poly alpha-1,3-glucan.

In an eighth embodiment, the acid catalyst in the method is an inorganic acid. The inorganic acid is sulfuric acid or perchloric acid in a ninth embodiment.

In a tenth embodiment, the acid anhydride in the method is one or more of acetic anhydride, propionic anhydride, or butyric anhydride; and the organic acid is one or more of acetic acid, propionic acid, or butyric acid. Non-limiting examples of this embodiment include:

(i) the acid anhydride is acetic anhydride, and the organic acid is acetic acid, wherein the poly alpha-1,3-glucan ester compound produced in the reaction is a poly alpha-1,3-glucan acetate;

(ii) the acid anhydrides are propionic anhydride and acetic anhydride, and the organic acids are propionic acid and optionally acetic acid, wherein the poly alpha-1,3-glucan ester compound produced in the reaction is a poly alpha-1,3-glucan acetate propionate;

(iii) the acid anhydride is propionic anhydride, and the organic acids are propionic acid and acetic acid, wherein the poly alpha-1,3-glucan ester compound produced in the reaction is a poly alpha-1,3-glucan acetate propionate;

(iv) the acid anhydrides are butyric anhydride and acetic anhydride, and the organic acids are butyric acid and optionally acetic acid, wherein the poly alpha-1,3-glucan ester compound produced in the reaction is a poly alpha-1,3-glucan acetate butyrate; and (v) the acid anhydride is butyric anhydride, and the organic acids are butyric acid and acetic acid, wherein the poly alpha-1,3-glucan ester compound produced in the reaction is a poly alpha-1,3-glucan acetate butyrate.

In an eleventh embodiment, the reaction further comprises an organic solvent.

In a twelfth embodiment, the contacting step of the method comprises:

(i) cooling the reaction;

(ii) cooling a mixture containing the poly alpha-1,3-glucan, acid catalyst and organic acid, and then adding the acid anhydride to the mixture;

(iii) cooling a mixture containing the acid anhydride and organic acid, and then adding the poly alpha-1,3-glucan and acid catalyst to the mixture; or (iv) cooling a mixture containing the acid catalyst and organic acid, and then adding the poly alpha-1,3-glucan and acid anhydride to the mixture.

In a thirteenth embodiment, the poly alpha-1,3-glucan ester compound produced in the reaction is poly alpha-1,3-glucan triacetate. The method in this embodiment further comprises: isolating the poly alpha-1,3-glucan triacetate; contacting the poly alpha-1,3-glucan triacetate with acetic acid and water to form a preparation; and applying steam pressure of about 3-10 kg/cm$^2$ to the preparation to raise its temperature up to 260° C., wherein poly alpha-1,3-glucan acetate is produced having a degree of substitution of 0.05 to 2.70. Poly alpha-1,3-glucan acetate produced by this method can optionally be isolated.

DETAILED DESCRIPTION OF INVENTION

The disclosures of all patent and non-patent literature cited herein are incorporated herein by reference in their entirety.

As used herein, the term "invention" or "disclosed invention" is not meant to be limiting, but applies generally to any of the inventions defined in the claims or described herein. These terms are used interchangeably herein.

The terms "poly alpha-1,3-glucan", "alpha-1,3-glucan polymer" and "glucan polymer" are used interchangeably herein. Poly alpha-1,3-glucan is a polymer comprising glucose monomeric units linked together by glycosidic linkages, wherein at least about 50% of the glycosidic linkages are alpha-1,3-glycosidic linkages. Poly alpha-1,3-glucan is a type of polysaccharide. The structure of poly alpha-1,3-glucan can be illustrated as follows:

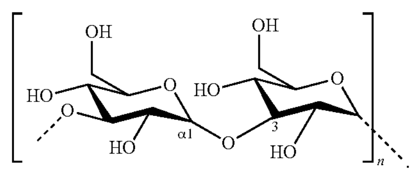

The poly alpha-1,3-glucan that can be used for preparing poly alpha-1,3-glucan ester compounds herein can be prepared using chemical methods. Alternatively, it can be prepared by extracting it from various organisms, such as fungi, that produce poly alpha-1,3-glucan. Alternatively still, poly alpha-1,3-glucan can be enzymatically produced from sucrose using one or more glucosyltransferase (gtf) enzymes (e.g., gtfJ), such as described in U.S. Pat. No. 7,000,000, and U.S. Patent Appl. Publ. Nos. 2013/0244288 and 2013/0244287 (all of which are incorporated herein by reference), for example.

The terms "glucosyltransferase enzyme", "gtf enzyme", "gtf enzyme catalyst", "gtf", and "glucansucrase" are used interchangeably herein. The activity of a gtf enzyme herein catalyzes the reaction of sucrose substrate to make products poly alpha-1,3-glucan and fructose. Other products (byproducts) of a gtf reaction can include glucose (where glucose is hydrolyzed from the glucosyl-gtf enzyme intermediate complex), various soluble oligosaccharides (DP2-DP7), and leucrose (where glucose of the glucosyl-gtf enzyme intermediate complex is linked to fructose). Leucrose is a disaccharide composed of glucose and fructose linked by an alpha-1,5 linkage. Wild type forms of glucosyltransferase enzymes generally contain (in the N-terminal to C-terminal direction) a signal peptide, a variable domain, a catalytic domain, and a glucan-binding domain. A gtf herein is classified under the glycoside hydrolase family 70 (GH70) according to the CAZy (Carbohydrate-Active EnZymes) database (Cantarel et al., *Nucleic Acids Res.* 37:D233-238, 2009).

The percentage of glycosidic linkages between the glucose monomer units of poly alpha-1,3-glucan used to prepare poly alpha-1,3-glucan ester compounds herein that are alpha-1,3 is at least about 50%, 60%, 70%, 80%, 90%, 95%, 96%, 97%, 98%, 99% or 100% (or any integer value between 50% and 100%). In such embodiments, accordingly, poly alpha-1,3-glucan has less than about 50%, 40%, 30%, 20%, 10%, 5%, 4%, 3%, 2%, 1%, or 0% (or any integer value between 0% and 50%) of glycosidic linkages that are not alpha-1,3.

Poly alpha-1,3-glucan used to produce poly alpha-1,3-glucan ester compounds herein is preferably linear/unbranched. In certain embodiments, poly alpha-1,3-glucan has no branch points or less than about 10%, 9%, 8%, 7%, 6%, 5%, 4%, 3%, 2% or 1% branch points as a percent of the glycosidic linkages in the polymer. Examples of branch points include alpha-1,6 branch points, such as those present in mutan polymer.

The terms "glycosidic linkage" and "glycosidic bond" are used interchangeably herein and refer to the type of covalent bond that joins a carbohydrate (sugar) molecule to another group such as another carbohydrate. The term "alpha-1,3-glycosidic linkage" as used herein refers to the type of covalent bond that joins alpha-D-glucose molecules to each other through carbons 1 and 3 on adjacent alpha-D-glucose rings. This linkage is illustrated in the poly alpha-1,3-glucan structure provided above. Herein, "alpha-D-glucose" is referred to as "glucose".

The terms "poly alpha-1,3-glucan ester compound", "poly alpha-1,3-glucan ester", and "poly alpha-1,3-glucan ester derivative" are used interchangeably herein. A poly alpha-1,3-glucan ester compound herein can be represented by the structure:

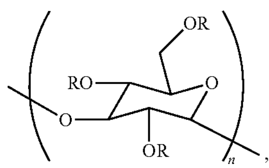

Regarding the formula of this structure, n can be at least 6, and each R can independently be a hydrogen atom (H) or an acyl group. A poly alpha-1,3-glucan ester compound herein has a degree of substitution of about 0.05 to about 3.0.

Poly alpha-1,3-glucan ester compounds disclosed herein are synthetic, man-made compounds.

A poly alpha-1,3-glucan ester compound is termed an "ester" herein by virtue of comprising the substructure —$C_G$—O—CO—C—, where "—$C_G$—" represents carbon 2, 4, or 6 of a glucose monomeric unit of a poly alpha-1,3-glucan ester compound, and where "—CO—C—" is comprised in the acyl group.

An "acyl group" herein can be an acetyl group (—CO—$CH_3$), propionyl group (—CO—$CH_2$—$CH_3$), butyryl group (—CO—$CH_2$—$CH_2$—$CH_3$), pentanoyl group (—CO—$CH_2$—$CH_2$—$CH_2$—$CH_3$), hexanoyl group (—CO—$CH_2$—$CH_2$—$CH_2$—$CH_2$—$CH_3$), heptanoyl group (—CO—$CH_2$—$CH_2$—$CH_2$—$CH_2$—$CH_2$—$CH_3$), or octanoyl group (—CO—$CH_2$—$CH_2$—$CH_2$—$CH_2$—$CH_2$—$CH_2$—$CH_3$), for example. The carbonyl group (—CO—) of the acyl group is ester-linked to carbon 2, 4, or 6 of a glucose monomeric unit of a poly alpha-1,3-glucan ester compound.

Regarding nomenclature, a poly alpha-1,3-glucan ester compound can be referenced herein by referring to the organic acid(s) corresponding with the acyl group(s) in the compound. For example, an ester compound comprising acetyl groups can be referred to as a poly alpha-1,3-glucan acetate, an ester compound comprising propionyl groups can be referred to as a poly alpha-1,3-glucan propionate, and an ester compound comprising butyryl groups can be referred to as a poly alpha-1,3-glucan butyrate. However, this nomenclature is not meant to refer to the poly alpha-1,3-glucan ester compounds herein as acids per se.

"Poly alpha-1,3-glucan triacetate" herein refers to a poly alpha-1,3-glucan ester compound with a degree of substitution by acetyl groups of 2.75 or higher.

The terms "poly alpha-1,3-glucan monoester" and "monoester" are used interchangeably herein. A poly alpha-1,3-glucan monoester contains only one type of acyl group. Examples of such monoesters are poly alpha-1,3-glucan acetate (comprises acetyl groups) and poly alpha-1,3-glucan propionate (comprises propionyl groups).

The terms "poly alpha-1,3-glucan mixed ester" and "mixed ester" are used interchangeably herein. A poly alpha-1,3-glucan mixed ester contains two or more types of an acyl group. Examples of such mixed esters are poly alpha-1,3-glucan acetate propionate (comprises acetyl and propionyl groups) and poly alpha-1,3-glucan acetate butyrate (comprises acetyl and butyryl groups).

The terms "reaction", "reaction composition", and "esterification reaction" are used interchangeably herein and refer to a reaction comprising poly alpha-1,3-glucan, at least one acid catalyst, at least one acid anhydride and at least one organic acid. The reaction is substantially anhydrous. A reaction is placed under suitable conditions (e.g., time, temperature) for esterification of one or more hydroxyl groups of the glucose units of poly alpha-1,3-glucan with an acyl group from at least the acid anhydride, thereby yielding a poly alpha-1,3-glucan ester compound.

The terms "substantially anhydrous" and "anhydrous" are used interchangeably herein. Substantially anhydrous conditions are conditions in which there is less than about 1.5 wt % or 2.0 wt % water. Such conditions may characterize a reaction or a reaction component, for example.

Herein, a poly alpha-1,3-glucan that is "acid-exchanged" has been treated with acid to remove water from the poly alpha-1,3-glucan. An acid-exchange process for producing acid-exchanged poly alpha-1,3-glucan can comprise one or more treatments in which the glucan is placed in an acid (e.g., organic acid) and then removed from the acid.

The term "acid catalyst" as used herein refers to any acid that accelerates progress of an esterification reaction. Examples of acid catalysts are inorganic acids such as sulfuric acid ($H_2SO_4$) and perchloric acid ($HClO_4$).

The term "acid anhydride" as used herein refers to an organic compound that has two acyl groups bound to the same oxygen atom. Typically, an acid anhydride herein has the formula $(R—CO)_2O$, where R is a saturated linear carbon chain (up to seven carbon atoms). Examples of acid anhydrides are acetic anhydride [$(CH_3—CO)_2O$], propionic anhydride [$(CH_3—CH_2—CO)_2O$] and butyric anhydride [$(CH_3—CH_2—CH_2—CO)_2O$].

The terms "organic acid" and "carboxylic acid" are used interchangeably herein. An organic acid has the formula R—COOH, where R is an organic group and COOH is a carboxylic group. The R group herein is typically a saturated linear carbon chain (up to seven carbon atoms). Examples of organic acids are acetic acid ($CH_3$—COOH), propionic acid ($CH_3$—$CH_2$—COOH) and butyric acid ($CH_3$—$CH_2$—$CH_2$—COOH).

The term "degree of substitution" (DoS) as used herein refers to the average number of hydroxyl groups substituted in each monomeric unit (glucose) of a poly alpha-1,3-glucan ester compound. Since there are three hydroxyl groups in each monomeric unit in poly alpha-1,3-glucan, the DoS in a poly alpha-1,3-glucan ester compound herein can be no higher than 3.

"Contacting" herein can be performed by any means known in the art, such as dissolving, mixing, shaking, or homogenization, for example. Where three or more reaction components are contacted with each other, such contacting can be done all at once or in stages (e.g., two components mixed before mixing in a third component).

The "molecular weight" of poly alpha-1,3-glucan and poly alpha-1,3-glucan ester compounds herein can be represented as number-average molecular weight ($M_n$) or as weight-average molecular weight ($M_w$). Alternatively, molecular weight can be represented as Daltons, grams/mole, DPw (weight average degree of polymerization), or DPn (number average degree of polymerization). Various means are known in the art for calculating these molecular weight measurements, such as high-pressure liquid chromatography (HPLC), size exclusion chromatography (SEC), or gel permeation chromatography (GPC).

The terms "percent by volume", "volume percent", "vol %" and "v/v %" are used interchangeably herein. The percent by volume of a solute in a solution can be determined using the formula: [(volume of solute)/(volume of solution)]×100%.

The terms "percent by weight", "weight percentage (wt %)" and "weight-weight percentage (% w/w)" are used interchangeably herein. Percent by weight refers to the percentage of a material on a mass basis as it is comprised in a composition, mixture or solution.

The terms "increased", "enhanced" and "improved" are used interchangeably herein. These terms may refer to, for example, a quantity or activity that is at least 1%, 2%, 3%, 4%, 5%, 6%, 7%, 8%, 9%, 10%, 20%, 30%, 40%, 50%, 60%, 70%, 80%, 90%, 100%, 125%, 150%, 175%, or 200% (or any integer between 1% and 200%) more than the quantity or activity for which the increased quantity or activity is being compared.

Embodiments of the disclosed invention concern a composition comprising a poly alpha-1,3-glucan ester compound represented by the structure:

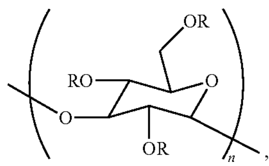

Regarding the formula of this structure, n can be at least 6, and each R can independently be an H or an acyl group. Furthermore, the poly alpha-1,3-glucan ester compound has a degree of substitution of about 0.05 to about 3.0.

Each R group in the formula of the poly alpha-1,3-glucan ester compound can independently be an H or an acyl group. An acyl group herein can be an acetyl group, propionyl group, butyryl group, pentanoyl group, hexanoyl group, heptanoyl group, or octanoyl group, for example. Thus, an acyl group can comprise a chain of 2 to 8 carbons; this chain preferably has no branches.

Poly alpha-1,3-glucan ester compounds in certain embodiments disclosed herein may contain one type of acyl group. For example, one or more R groups ester-linked to the glucose group in the above formula may be a propionyl group; the R groups in this particular example would thus independently be hydrogen and propionyl groups. As another example, one or more R groups ester-linked to the glucose group in the above formula may be an acetyl group; the R groups in this particular example would thus independently be hydrogen and acetyl groups. Certain embodiments of poly alpha-1,3-glucan ester compounds herein do not have a DoS by acetyl groups of 2.75 or more.

Alternatively, poly alpha-1,3-glucan ester compounds disclosed herein can contain two or more different types of acyl groups. Examples of such compounds contain two different acyl groups, such as (i) acetyl and propionyl groups (poly alpha-1,3-glucan acetate propionate, where R groups are independently H, acetyl, or propionyl), or (ii) acetyl and butyryl groups (poly alpha-1,3-glucan acetate butyrate, where R groups are independently H, acetyl, or butyryl).

The poly alpha-1,3-glucan ester compound has a degree of substitution (DoS) of about 0.05 to about 3.0. Alternatively, the DoS of a poly alpha-1,3-glucan ester compound disclosed herein can be about 0.2 to about 2.0. Alternatively still, the DoS can be at least about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0. It would be understood by those skilled in the art that since a poly alpha-1,3-glucan ester compound disclosed herein has a degree of substitution between about 0.05 to about 3.0, the R groups of the compound cannot only be hydrogen.

The wt % of one or more acyl groups in a poly alpha-1,3-glucan ester compound herein can be referred to instead of referencing a DoS value. For example, the wt % of an acyl group in a poly alpha-1,3-glucan ester compound can be at least about 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60%.

The percentage of glycosidic linkages between the glucose monomer units of the poly alpha-1,3-glucan ester compound that are alpha-1,3 is at least about 50%, 60%, 70%, 80%, 90%, 95%, 96%, 97%, 98%, 99%, or 100% (or any integer between 50% and 100%). In such embodiments, accordingly, the compound has less than about 50%, 40%, 30%, 20%, 10%, 5%, 4%, 3%, 2%, 1%, or 0% (or any integer value between 0% and 50%) of glycosidic linkages that are not alpha-1,3.

The backbone of a poly alpha-1,3-glucan ester compound disclosed herein is preferably linear/unbranched. In certain embodiments, the compound has no branch points or less than about 10%, 9%, 8%, 7%, 6%, 5%, 4%, 3%, 2%, or 1% branch points as a percent of the glycosidic linkages in the polymer. Examples of branch points include alpha-1,6 branch points.

The formula of a poly alpha-1,3-glucan ester compound in certain embodiments can have an n value of at least 6. Alternatively, n can have a value of at least 10, 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, or 4000 (or any integer between 10 and 4000).

The molecular weight of a poly alpha-1,3-glucan ester compound disclosed herein can be measured as number-average molecular weight ($M_n$) or as weight-average molecular weight ($M_w$). Alternatively, molecular weight can be measured in Daltons or grams/mole. It may also be useful to refer to the $DP_w$ (weight average degree of polymerization) or $DP_n$ (number average degree of polymerization) of the poly alpha-1,3-glucan polymer component of the compound.

The $M_n$ or $M_w$ of poly alpha-1,3-glucan ester compounds disclosed herein may be at least about 1000. Alternatively, the $M_n$ or $M_w$ can be at least about 1000 to about 600000. Alternatively still, the $M_n$ or $M_w$ can be at least about 10000, 25000, 50000, 75000, 100000, 125000, 150000, 175000, 200000, 225000, 250000, 275000, or 300000 (or any integer between 10000 and 300000), for example.

A poly alpha-1,3-glucan ester in certain embodiments can have a DoS by acetyl groups up to about 2.00, 2.05, 2.10, 2.15, 2.20, 2.25, 2.30, 2.35, 2.40, 2.45, 2.50, 2.55, 2.60, 2.65, 2.70, 2.75, 2.80, 2.85, 2.90, 2.95, or 3.00. Thus, for example, the DoS by acetyl groups can be up to about 2.00-2.40, 2.00-2.50, or 2.00-2.65. As other examples, the DoS by acetyl groups can be about 0.05 to about 2.60, about 0.05 to about 2.70, about 1.2 to about 2.60, or about 1.2 to about 2.70. Such poly alpha-1,3-glucan esters can be a monoester or a mixed ester.

A poly alpha-1,3-glucan ester in certain embodiments can have a wt % of propionyl groups up to about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, or 55%. Such poly alpha-1,3-glucan esters can be a monoester or a mixed ester. Regarding mixed esters, poly alpha-1,3-glucan acetate propionate can have a wt % of acetyl groups up to about 0.1%, 1%, 2%, 3%, 4%, 5%, 6%, 7%, 8%, 9%, or 10%, and a wt % of propionyl groups as per any of the propionyl wt %'s listed above, for example.

A poly alpha-1,3-glucan ester in certain embodiments can have a wt % of butyryl groups up to about 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60%. A poly alpha-1,3-glucan ester in other embodiments can have a DoS by butyryl groups up to about 0.80, 0.85, 0.90, 0.95, 1.00, 1.05, 1.10, 1.15, or 1.20. Such poly alpha-1,3-glucan esters can be a monoester or a mixed ester. Regarding mixed esters, poly alpha-1,3-glucan acetate butyrate can have a wt % of acetyl groups up to about 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, or 36%, and a wt % of butyryl groups as per any of the butyryl wt %'s listed above, for example.

The disclosed invention also concerns a method for producing a poly alpha-1,3-glucan ester compound. This method comprises: contacting poly alpha-1,3-glucan in a reaction that is substantially anhydrous with at least one acid catalyst, at least one acid anhydride, and at least one organic acid, wherein an acyl group derived from the acid anhydride is esterified to the poly alpha-1,3-glucan thereby producing a poly alpha-1,3-glucan ester compound represented by the structure:

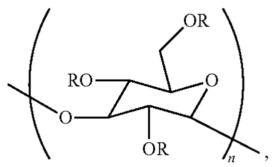

wherein (i) n is at least 6, (ii) each R is independently an H or the acyl group, and (iii) the compound has a degree of substitution of about 0.05 to about 3.0.

A poly alpha-1,3-glucan ester produced by this method can optionally be isolated.

A poly alpha-1,3-glucan is contacted with at least one acid catalyst, at least one acid anhydride, and at least one organic acid in a reaction that is substantially anhydrous. A substantially anhydrous reaction herein contains no water or less than about 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 wt % water. Substantially anhydrous conditions can be obtained by using reaction components that are substantially anhydrous. Reaction components that are not substantially anhydrous may be used for preparing a reaction, but only in amounts such that the final reaction preparation is substantially anhydrous.

Enzymatically produced preparations of poly alpha-1,3-glucan that can be used in the disclosed esterification reaction typically contain water. This poly alpha-1,3-glucan can be acid-exchanged to remove water thereby rendering the glucan to be substantially anhydrous. In certain embodiments, poly alpha-1,3-glucan can be acid-exchanged with an organic acid (e.g., acetic, propionic, or butyric acid) before contacting step (a) to remove water from the poly alpha-1,3-glucan. An acid-exchange process herein can comprise boiling poly alpha-1,3-glucan in water, removing most of the water by any physical means (e.g., filtration, decantation, and/or drying), placing the glucan in an organic acid, and then removing the organic acid by filtration and/or decantation. Treatment with an organic acid can comprise stirring the glucan in the acid, and can be performed one, two, or more times. The amount of organic acid used in each treatment can be at least about 2 to 20 times, or 2 to 10 times, the amount of poly alpha-1,3-glucan being treated, for example.

Poly alpha-1,3-glucan is contacted with at least one acid catalyst in the disclosed reaction. An acid catalyst can be an inorganic acid in certain embodiments. Examples of an inorganic acid catalyst that can be included in a reaction herein are sulfuric acid and perchloric acid. Other examples of inorganic acid catalysts include hydrochloric, phosphoric, nitric, boric, hydrofluoric, hydrobromic, sulfonic, any mineral acid, and any combination thereof. An acid catalyst herein can typically be obtained commercially in a concentrated (e.g., >95%, 96%, 97%, 98%, or 99% pure) and/or substantially anhydrous form. For example, sulfuric acid for use in a reaction herein can be at least about 95-98% pure. Alternatively, an acid catalyst can be provided in solution with an organic acid such as acetic acid. An example of such a solution is perchloric acid (0.1 N) in acetic acid. The amount of acid catalyst in a reaction can be at least about 0.005, 0.0075, 0.01, 0.025, 0.05, 0.075, 0.1, 0.25, 0.5, 0.75, 1.0, 1.25, 1.5, 1.75, or 2.0 wt %, for example.

Poly alpha-1,3-glucan is contacted with at least one acid anhydride in the disclosed reaction. Examples of an acid anhydride that can be included in a reaction herein include acetic anhydride, propionic anhydride, butyric anhydride, pentanoic anhydride, hexanoic anhydride, heptanoic anhydride, octanoic anhydride and phthalic anhydride. Any combination of these can be used in a reaction herein (e.g., acetic and propionic anhydrides, acetic and butyric anhydrides, propionic and butyric anhydrides). An acid anhydride herein can typically be obtained commercially in a concentrated (e.g., >95%, 96%, 97%, 98%, or 99% pure) and/or substantially anhydrous form. For example, acetic anhydride, propionic anhydride and/or butyric anhydride for use in a reaction herein can be at least about 97%, 98%, or 99% pure. The amount of acid anhydride in a reaction can be at least about 10, 15, 20, 25, 30, 35, 40, 45, 50, 55, 60, 65, or 70 wt % (or any integer value between 10 and 70 wt %), for example. In certain embodiments, the amount of acetic anhydride in a reaction can be at least about 20-45 wt %. The amount of propionic or butyric anhydride in other embodiments can be at least about 40-50 wt %.

Poly alpha-1,3-glucan is contacted with at least one organic acid in the disclosed reaction. Examples of an organic acid that can be included in a reaction herein include acetic acid, propionic acid, butyric acid, pentanoic acid, hexanoic acid, heptanoic acid, octanoic acid and phthalic acid. The amount of organic acid in a reaction can be at least about 5, 10, 15, 20, 25, 30, 35, 40, 45, 50, 55, 60, 65, 70, 75, or 80 wt % (or any integer value between 5 and 80 wt %), for example.

Typically, one or more acid anhydrides used in a reaction herein are selected based on the type of esterification desired. As examples, if esterification of poly alpha-1,3-glucan with acetyl groups, propionyl groups and/or butyryl groups is desired, then acetic anhydride, propionic anhydride and/or butyric anhydride, respectively, is/are included in the reaction accordingly. The selected acid anhydride(s) is the main source of acyl groups in the disclosed esterification process. That being said, acyl groups for esterification can also be derived from one or more organic acids included in the reaction. For example, an acetyl group, propionyl group, butyryl group, pentanoyl group, hexanoyl group, heptanoyl group, and octanoyl group can be derived from, respectively, acetic acid, propionic acid, butyric acid, pentanoic acid, hexanoic acid, heptanoic acid, and octanoic acid. Reactions containing a particular acid anhydride typically also contain the organic acid corresponding to the acid anhydride.

In certain embodiments of the disclosed reaction, the acid anhydride is one or more of acetic anhydride, propionic anhydride, or butyric anhydride; and the organic acid is one or more of acetic acid, propionic acid, or butyric acid. Combinations of (i) acetic anhydride and acetic acid can be used to prepare poly alpha-1,3-glucan acetate; (ii) propionic anhydride and propionic acid can be used to prepare poly alpha-1,3-glucan propionate; (iii) butyric anhydride and butyric acid can be used to prepare poly alpha-1,3-glucan butyrate; (iv) propionic anhydride, propionic acid, acetic anhydride and optionally acetic acid can be used to prepare poly alpha-1,3-glucan acetate propionate; (v) propionic anhydride, propionic acid and acetic acid can be used to prepare poly alpha-1,3-glucan acetate propionate; (vi) butyric anhydride, butyric acid, acetic anhydride and optionally acetic acid can be used to prepare poly alpha-1,3-glucan acetate butyrate; and (vii) butyric anhydride, butyric acid and acetic acid can be used to prepare poly alpha-1,3-glucan acetate butyrate, for example. In reactions containing acetic acid along with propionic acid or butyric acid, the amount of acetic acid can be about 5-10, 5-20, or 5-30 wt %, for example.

Reactions for producing mixed esters (e.g., poly alpha-1,3-glucan acetate propionate, poly alpha-1,3-glucan acetate butyrate) typically contain more of an acid anhydride having an acyl group for which a higher DoS is desired, and less of an acid anhydride and/or corresponding organic acid for which a lower DoS is desired. For example, to produce a poly alpha-1,3-glucan acetate propionate with a higher DoS of propionyl groups compared to acetyl groups, more propionic anhydride is included in a reaction compared to the amount of acetic anhydride and/or acetic acid. DoS in mixed esters may also be modulated by the order in which acid anhydrides are added to a reaction already containing an acid catalyst. For example, one may expect a higher DoS with propionyl groups if propionic anhydride is added before acetic anhydride (to a preparation already containing acid catalyst) when preparing a reaction to produce poly alpha-1,3-glucan acetate propionate.

An acid anhydride selected for a reaction herein can correspond with the organic acid used to prepare acid-exchanged poly alpha-1,3-glucan. For example, if a reaction will include propionic anhydride, then an acid exchange process can be performed with propionic acid. Alternatively, an acid anhydride selected for a reaction herein can differ from the organic acid used to prepare acid-exchanged poly alpha-1,3-glucan. For example, if a reaction will include propionic anhydride, then an acid exchange process can be performed with acetic acid.

A reaction herein can comprise components in addition to poly alpha-1,3-glucan, acid catalyst, acid anhydride, and organic acid. For example, one or more organic solvents can be included in a reaction, such as methylene chloride. An organic solvent such a methylene chloride can be included at about 30-40 wt % in a reaction (e.g., producing glucan triacetate), for example.

The components of a reaction herein can be added together in any order. For example, poly alpha-1,3-glucan, acid catalyst and organic acid can first be mixed together, afterwhich acid anhydride can be added to the mixture. As another example, acid anhydride and organic acid can first be mixed together, afterwhich poly alpha-1,3-glucan and acid catalyst can be added to the mixture. As yet another example, acid catalyst and organic acid can first be mixed together, afterwhich poly alpha-1,3-glucan and acid anhydride can be added to the mixture. In certain embodiments, poly alpha-1,3-glucan and another component (e.g., acid catalyst or acid anhydride) are added in sequential order to a mixture containing the other reaction components.

Cooling can be applied during various stages of preparing a reaction herein. The terms “cool” and “chill” are used interchangeably herein and refer to decreasing the temperature of a reaction or mixture to a lower temperature. Cooling can be performed by any means known in the art, such as with an ice bath or industrial cooling system. Step (a) of preparing a reaction can comprise cooling the reaction after its preparation (i.e., containing all of poly alpha-1,3-glucan, acid catalyst, acid anhydride and organic acid), such as to about 10, 11, 12, 13, 14, 15, 16, 17, 18, 19, or 20° C., or about 12-18° C. Alternatively, step (a) can comprise cooling (e.g., to any of the preceding temperatures) a mixture containing poly alpha-1,3-glucan, acid catalyst and organic acid, and then adding acid anhydride to the cooled mixture. Alternatively still, step (a) can comprise cooling (e.g., to any of the preceding temperatures) a mixture containing acid anhydride and organic acid, and then adding poly alpha-1,3-glucan and acid catalyst to the cooled mixture. Alternatively still, step (a) can comprise cooling (e.g., to any of the preceding temperatures) a mixture containing acid catalyst and organic acid, and then adding poly alpha-1,3-glucan and acid anhydride to the cooled mixture. A reaction can optionally be held at any of the preceding cooler temperature points for about 1-10 minutes after its initial preparation.

A reaction can then be (i) placed under ambient temperature conditions without direct application of heat, and/or (ii) directly heated using any means known in the art (e.g., water bath, industrial or electric heater). Ambient temperature conditions can be held for up to about 30, 60, 120, 240, 360, or 480 minutes (or any integer value between 30 and 480 minutes), for example. Alternatively, ambient temperature conditions can be held for up to about 24, 48, or 72 hours. The term “ambient temperature” as used herein refers to a temperature between about 15-30° C. or 20-25° C. (or any integer between 15 and 30° C.). Reaction heating can be up to about 30, 35, 40, 45, 50, 55, 60, 65, 70, 75, or 80° C. (or any integer value between 30 and 80° C.), about 30-60° C., or about 30-50° C., for example. Such heating can be done is stages, if desired. For example, a reaction can first be heated to about 35° C., and then heated to about 39-50° C. A maximum reaction temperature (e.g., about 36-43° C.) may be applied to avoid excess degradation of poly alpha-1,3-glucan ester molecular weight in certain embodiments, such as when producing poly alpha-1,3-glucan propionate, poly alpha-1,3-glucan acetate propionate, or poly alpha-1,3-glucan acetate butyrate. The temperature after heating to any of the preceding temperatures can be maintained for about 20-30, 20-40, 20-60 minutes, or up to about 40, 60, 80, 100, 120, or 140 minutes, for example. When heating is done in stages, the first temperature point(s) can be held for about 20-40 minutes, for example. In embodiments in which a reaction is placed under ambient temperature conditions without direct application of heat, the reaction can subsequently be heated, if desired, to any of the preceding temperatures and time periods. A reaction typically does not contain any solid material, but may be viscous, after any of the above temperature treatments (ambient temperature and/or heating).

A reaction can optionally be cooled after any of the above temperature treatments (ambient temperature and/or heating). For example, a reaction can be cooled to about 18, 19, 20, 21, 22, 23, 24, or 25° C., about 20-30° C., or about 20-40° C. A reaction that was heated to 60-80° C. can typically be cooled to about 35-45° C. The temperature of a reaction upon cooling can be held for about 5-10 minutes, for example.

Optionally, a reaction herein can be maintained under an inert gas (e.g., nitrogen). As used herein, the term "inert gas" refers to a gas which does not undergo chemical reactions under a set of given conditions; such as those disclosed for preparing a reaction herein.

A reaction can optionally be quenched after any of the above temperature treatments (ambient temperature and/or heating) and cooling treatments. Quenching of a reaction can be accomplished by adding acid, base, or certain salts to the reaction. Various acids, bases and salts useful for quenching a reaction include, but are not limited to, acetic acid (e.g., ~50-70 wt %), any other mineral or organic acid (e.g., ~50-70 wt %), magnesium acetate (e.g., ~20-25 wt %), sodium hydroxide, potassium hydroxide, calcium hydroxide, sodium bicarbonate, sodium carbonate and combinations thereof. In certain embodiments of producing poly alpha-1,3-glucan acetate, a reaction is quenched with acetic acid (e.g., ~50 or 70 wt %) or magnesium acetate (e.g., ~20-25 wt %).

A quenched reaction can optionally be heated to about 40° C. to 150° C. for up to 48 hours. For example, a quenched reaction can be heated to about 100° C. for up to about 20-40 minutes (e.g., 25-30 minutes), such as in a process for producing poly alpha-1,3-glucan acetate. Optionally, water may be added to a reaction (quenched or not quenched), which is then heated to about 40° C. to 150° C. (e.g., ~100° C.) for up to about 20-40 minutes (e.g., 25-30 minutes) to reduce DoS of acyl groups by hydrolysis. Such a heating/water-treatment step may be useful for reducing DoS in a process for producing poly alpha-1,3-glucan acetate.

A poly alpha-1,3-glucan ester compound produced by a reaction herein can be precipitated using an agent that is a non-solvent for the poly alpha-1,3-glucan ester compound. For example, deionized water and/or methanol can be added to a reaction solution in an amount sufficient to precipitate a poly alpha-1,3-glucan ester compound. Precipitation herein can further comprise mixing the reaction solution and non-solvent by any means known in the art, such as with an air-powered blender.

Precipitated poly alpha-1,3-glucan ester compound can optionally be neutralized by washing it with water two or more times, followed by a wash in a bicarbonate (e.g., sodium bicarbonate) solution (e.g., ~5 wt %). The ester compound can then be washed one, two or more times with water until neutral pH is achieved. Alternatively, precipitated poly alpha-1,3-glucan ester compound can be washed with water and base (e.g., diluted alkaline hydroxide such as sodium hydroxide, calcium hydroxide, or potassium hydroxide) to achieve a neutral pH, optionally followed by washing with water. The term "neutral pH" as used herein refers to a pH that is neither substantially acidic or basic (e.g., a pH of about 6-8, or about 6.0, 6.2, 6.4, 6.6, 6.8, 7.0, 7.2, 7.4, 7.6, 7.8, or 8.0).

A poly alpha-1,3-glucan ester produced in the disclosed reaction can be isolated. The above precipitation process can be a step in an isolation process. Isolation can be performed with precipitated product before or after neutralization and/or washing steps using a funnel, centrifuge, press filter, or any other method or equipment known in the art that allows removal of liquids from solids. An isolated poly alpha-1,3-glucan ester product can be dried using any method known in the art, such as vacuum drying, air drying (e.g., ~16-35° C.), or freeze drying.

Any of the above esterification reactions can be repeated using a poly alpha-1,3-glucan ester product as the starting material for further modification. This approach may be suitable for increasing the DoS of an acyl group, and/or adding one or more different acyl groups to the ester product.

The structure, molecular weight and DoS of a poly alpha-1,3-glucan ester product can be confirmed using various physiochemical analyses known in the art such as NMR spectroscopy and size exclusion chromatography (SEC).

The percentage of glycosidic linkages between the glucose monomer units of poly alpha-1,3-glucan used to prepare poly alpha-1,3-glucan ester compounds herein that are alpha-1,3 is at least about 50%, 60%, 70%, 80%, 90%, 95%, 96%, 97%, 98%, 99%, or 100% (or any integer value between 50% and 100%). In such embodiments, accordingly, poly alpha-1,3-glucan has less than about 50%, 40%, 30%, 20%, 10%, 5%, 4%, 3%, 2%, 1%, or 0% (or any integer value between 0% and 50%) of glycosidic linkages that are not alpha-1,3.

Poly alpha-1,3-glucan used to prepare poly alpha-1,3-glucan ester compounds herein is preferably linear/unbranched. In certain embodiments, poly alpha-1,3-glucan has no branch points or less than about 10%, 9%, 8%, 7%, 6%, 5%, 4%, 3%, 2%, or 1% branch points as a percent of the glycosidic linkages in the polymer. Examples of branch points include alpha-1,6 branch points.

The $M_n$ or $M_w$ of poly alpha-1,3-glucan used to prepare poly alpha-1,3-glucan ester compounds herein may be at least about 500 to about 300000. Alternatively still, $M_n$ or $M_w$ can be at least about 10000, 25000, 50000, 75000, 100000, 125000, 150000, 175000, 200000, 225000, 250000, 275000, or 300000 (or any integer between 10000 and 300000), for example.

A process is disclosed herein for producing poly alpha-1,3-glucan acetate with a DoS of 0.05 to 2.70 using poly alpha-1,3-glucan triacetate. The triacetate used in this process can be produced according to any of the above processes, for example. This process comprises: contacting poly alpha-1,3-glucan triacetate with acetic acid and water to form a preparation, and applying steam pressure of about 3-10 kg/cm$^2$ to the preparation to raise its temperature up to about 260° C. This process results in a poly alpha-1,3-glucan acetate having a DoS of 0.05 to 2.70. Such reduction in DoS results from hydrolysis of a portion of the acetyl groups of the poly alpha-1,3-glucan triacetate. A poly alpha-1,3-glucan acetate produced by this method can optionally be isolated.

Poly alpha-1,3-glucan triacetate can optionally be washed and/or have a neutral pH prior to use in this process. Poly alpha-1,3-glucan triacetate can be contacted with acetic acid and water by first dissolving the glucan triacetate in acetic acid, and then adding water to this solution. In certain embodiments, the amount of acetic acid in the preparation can be about 75, 80, 85, or 90 wt %, and the amount of water in the preparation can be up to about 1, 2, 3, 4, 5, 6, 7, 8, 9, or 10 wt %.

A preparation containing poly alpha-1,3-glucan triacetate, acetic acid and water is then subjected to steam pressure of about 3-10 kg/cm$^2$ to raise its temperature up to about 260°

C. This step can be optionally be carried out in a pressure vessel such as a Parr reactor, autoclave, or any other pressure vessel known in the art. A steam pressure of about 4, 5, or 6 kg/$cm^2$, for example, can be used to raise the temperature of the preparation to about 140-160° C. (e.g., 150° C.). This elevated temperature can be held for about 30, 40, 50, 60, or 70 minutes, afterwhich the applied pressure can be increased further to about 7, 8, or 9 kg/$cm^2$. After reaching this elevated pressure, the temperature can be cooled to ambient temperature.

Poly alpha-1,3-glucan acetate having a DoS of 0.05 to 2.70 can be isolated from the pressure-/heat-treated preparation using any of the precipitation, washing and isolation steps disclosed above.

Poly alpha-1,3-glucan esters formed using various methods described above can be used to prepare various types of films. The poly alpha-1,3-glucan esters prepared according to the disclosed methods can be dissolved in one or more solvents to provide a solution of poly alpha-1,3-glucan ester. As used herein, the term "solution of poly alpha-1,3-glucan ester" refers to poly alpha-1,3-glucan ester dissolved in one or more solvents. The solvents useful for this purpose include, but are not limited to, methylene chloride (dichloromethane), methanol, chloroform, tetrachloroethane, formic acid, acetic acid, nitrobenzene, bromoform, pyridine, dioxane, ethanol, acetone, alcohols, aromatic compounds such as monochlorobenzene, benzene and toluene, esters such as ethyl acetate and propyl acetate, ethers such as tetrahydrofuran, methyl cellosolve and ethylene glycol monomethyl ether or combinations thereof. In an embodiment poly alpha-1,3-glucan acetate is dissolved in acetone to prepare a solution of poly alpha-1,3-glucan acetate. This solution can then be applied to a surface and the solvent is allowed to evaporate to form a film of desired thickness. The surfaces suitable for this application can be, but are not limited to, glass, Teflon®, plastic, or various types of substrates. Methods to make films from the above-mentioned solution, which are well known in the art, include but not limited to solution casting, spin coating, thermal and regular spraying. In an embodiment, the solution of poly alpha-1,3-glucan ester is cast on a glass plate.

The tear resistance, tensile strength and temperature stability of the poly alpha-1,3-glucan ester films can be determined by methods well known in the art. As used herein, the term "tear resistance" is defined as a measure of how well a film can withstand the effects of tearing. The term "tensile strength", as used herein, refers to the maximum tension a material can withstand without tearing. The suitable tear resistance for a poly alpha-1,3-glucan ester film disclosed herein can be at least 0.1 gf/mil. The tensile strength of the film suitable for the disclosed invention can be at least 10 kg/$mm^2$. In an embodiment, the tear resistance of the poly alpha-1,3-glucan diacetate film is 2-2.4 gf/mil and the tensile strength is 206-208 kg/$mm^2$. In another embodiment, the tear resistance is 1.4-3.1 gf/mil and the tensile strength is 39-203 kg/$mm^2$.

The haze and transmittance of the poly alpha-1,3-glucan ester film can be determined by methods well known in the art. As used herein, the term "haze" refers to the percentage of light that is deflected more than 2.5 degrees from the incoming light direction. Low haze values correspond to better clarity. The term "transmittance" as used herein, refers to the fraction of incident light at a specified wavelength that passes through a film. The suitable film for the poly alpha-1,3-glucan acetate film in this application can have a haze up to 20% and the transmittance of at least 80%. In an embodiment, the haze is 6.2% and the transmittance is 94.6%.

The speed with which the film is produced can be increased by adding a weak solvent, such as methanol and cyclohexane, ethanol and n-butanol or abundant methanol or ethanol in addition to methylene chloride, into the poly alpha-1,3-glucan ester solution to accelerate the solidification speed. One can restrain planar orientation degree and crystallization degree by controlling the surface temperature and shrinkage percentage of a film.

EXAMPLES

The disclosed invention is further defined in the following Examples. It should be understood that these Examples, while indicating certain preferred aspects of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Abbreviations:

"mL" is milliliter(s); "g" is gram(s); "DI water" is deionized water; "A" is microliter(s); "° C." is degrees Celsius; "mg" is milligram(s); "TFA" is trifluoroacetic acid; "Hz" is Hertz; "MHz" is mega Hertz; "ppm" is parts per million; "HFIP" is hexafluoro-2-propanol; "TFA-d" is deuterated trifluoroacetic acid.

Materials

Sulfuric acid, acetic acid and sodium bicarbonate were from EMD Chemicals (Billerica, Mass.). Acetic anhydride was from Acros Organics (Pittsburgh, Pa.). Butyric acid, butyric anhydride, propionic anhydride and 0.1 N perchloric acid in acetic acid were from Sigma Aldrich (St. Louis, Mo.). Propionic acid was from JT Baker (Center Valley, Pa.). Magnesium acetate was from Alfa Aesar (Ward Hill, Mass.). Unless otherwise specified, all acids and anhydrides used herein were water-free or substantially water-free.

Preparation of Poly Alpha-1,3-Glucan

Poly alpha-1,3-glucan was prepared using a gtfJ enzyme preparation as described in U.S. Patent Appl. Publ. No. 2013/0244288, which is incorporated herein by reference in its entirety.

$^1$H Nuclear Magnetic Resonance (NMR) Method for Determining Degree of Substitution of Poly Alpha-1,3-Glucan Acetate Derivatives Degree of substitution (DoS) in poly alpha-1,3-glucan acetate ester derivatives was determined using $^1$H NMR. Approximately 20 mg of derivative sample was weighed into a vial on an analytical balance. The vial was removed from the balance and 0.7 mL of TFA-d was added to the vial. A magnetic stir bar was added to the vial and the mixture was stirred until the solid sample dissolved. Deuterated benzene ($C_6D_6$), 0.3 mL, was then added to the vial to provide a better NMR lock signal than the TFA-d would provide. A portion, 0.8 mL, of the solution was transferred using a glass pipet into a 5-mm NMR tube. A quantitative $^1$H NMR spectrum was acquired using an Agilent VNMRS 400 MHz NMR spectrometer equipped with a 5-mm Autoswitchable Quad probe. The spectrum was acquired at a spectral frequency of 399.945 MHz using a spectral window of 6410.3 Hz, an acquisition time of 1.278 seconds, and an inter-pulse delay of 10 seconds and 124 pulses. The time domain data were transformed using exponential multiplication of 0.78 Hz.

Two regions of the resulting spectrum were integrated: from 3.1 ppm to 6.0 ppm, giving the integral for the seven poly alpha-1,3-glucan protons, and from 1.4 ppm to 2.7 ppm, giving the integral for the three acetyl protons. The degree of acetylation was calculated by dividing one third of the acetyl protons integral area by one seventh of the poly alpha-1,3-glucan protons integral area.

$^1$H NMR Method for Determining Degree of Substitution of Poly Alpha-1,3-Glucan Propionate Derivatives DoS in poly alpha-1,3-glucan propionate ester derivatives was determined using $^1$H NMR. Approximately 20 mg of derivative sample was weighed into a vial on an analytical balance. The vial was removed from the balance and 0.7 mL of TFA-d was added to the vial. A magnetic stir bar was added to the vial and the mixture was stirred until the solid sample dissolved. Deuterated benzene ($C_6D_6$), 0.3 mL, was then added to the vial to provide a better NMR lock signal than the TFA-d would provide. A portion, 0.8 mL, of the solution was transferred using a glass pipet into a 5-mm NMR tube. A quantitative $^1$H NMR spectrum was acquired using an Agilent VNMRS 400 MHz NMR spectrometer equipped with a 5-mm Autoswitchable Quad probe. The spectrum was acquired at a spectral frequency is 399.945 MHz using a spectral window of 6410.3 Hz, an acquisition time of 1.278 seconds, and an inter-pulse delay of 10 seconds and 32 pulses. The time domain data were transformed using exponential line broadening of 1.0 Hz and the benzene solvent peak was set to 7.15 ppm.

For poly alpha-1,3-glucan propionate samples, three regions of the resulting spectrum were integrated: from 3.3 ppm to 6.0 ppm, giving the integral for the seven poly alpha-1,3-glucan protons; from 1.9 ppm to 2.7 ppm, giving the integral for the methylene group of the propionyl group plus the methyl group of the acetyl group; and from 0.8 ppm to 1.3 ppm, giving the integral for the methyl group of the propionyl group.

The DoS by propionyl groups was calculated by dividing the integral value for the methyl group of the propionyl group by three. The integral value of the propionyl group's methylene group was then calculated by multiplying the integral value for the methyl group of the propionyl group by 0.666. This value was then subtracted from the integral for the region of the methylene group of the propionyl group plus the methyl group of the acetyl group to give the integral value for the acetyl group's methyl group.

$^1$H NMR Method for Determining Degree of Substitution of Poly Alpha-1,3-Glucan Mixed Ester Derivatives DoS in poly alpha-1,3-glucan mixed ester derivatives was determined using $^1$H NMR. Approximately 20 mg of derivative sample was weighed into a vial on an analytical balance. The vial was removed from the balance and 0.7 mL of TFA-d was added to the vial. A magnetic stir bar was added to the vial and the mixture was stirred until the solid sample dissolved. Deuterated benzene ($C_6D_6$), 0.3 mL, was then added to the vial to provide a better NMR lock signal than the TFA-d would provide. A portion, 0.8 mL, of the solution was transferred using a glass pipet into a 5-mm NMR tube. A quantitative $^1$H NMR spectrum was acquired using an Agilent VNMRS 400 MHz NMR spectrometer equipped with a 5-mm Autoswitchable Quad probe. The spectrum was acquired at a spectral frequency of 399.945 MHz using a spectral window of 6410.3 Hz, an acquisition time of 1.278 seconds, and inter-pulse delay of 10 seconds and 32 pulses. The time domain data were transformed using exponential line broadening of 1.0 Hz and the benzene solvent peak was set to 7.15 ppm.

For poly alpha-1,3-glucan acetate propionate samples, three regions of the resulting spectrum were integrated: from 3.3 ppm to 6.0 ppm, giving the integral for the seven poly alpha-1,3-glucan protons; from 1.9 ppm to 2.7 ppm giving the integral for the methylene group of the propionyl group plus the methyl group of the acetyl group; and from 0.8 ppm to 1.3 ppm giving the integral for the methyl group of the propionyl group.

The DoS by propionyl groups on the glucan was calculated by dividing the integral value for the methyl group of the propionyl group by three. The integral value of the propionyl group's methylene group was then calculated by multiplying the integral value for the methyl group of the propionyl group by 0.666. This value was then subtracted from the integral for the region of the methylene group of the propionyl group plus the methyl group of the acetyl group to give the integral value for the acetyl group's methyl group. Finally, the acetyl group integral value was divided by three to obtain the degree of acetylation.

For poly alpha-1,3-glucan acetate butyrate samples, three regions of the resulting spectrum were integrated: from 3.3 ppm to 6.0 ppm giving the integral for the seven poly alpha-1,3-glucan protons; from 1.9 ppm to 2.6 ppm giving the integral for the methylene group alpha to the carbonyl of the butyryl group plus the methyl group of the acetyl group; and from 0.6 ppm to 1.0 ppm giving the integral for the methyl group of the butyryl group.

The DoS by butyryl groups on the glucan was calculated by dividing the integral value for the methyl group of the butyryl group by three. The integral value of the butyryl group's methylene group was then calculated by multiplying the integral value for the methyl group of the butyryl group by 0.666. This value was then subtracted from the integral for the region of the methylene group of the butyryl group plus the methyl group of the acetyl group to give the integral value for the acetyl group's methyl group. Finally, the acetyl group integral value was divided by three to obtain the degree of acetylation.

Determination of the Degree of Polymerization

The degree of polymerization (DP) was determined by size exclusion chromatography (SEC). Poly alpha-1,3-glucan ester was dissolved in HFIP (2 mg/mL) with shaking for 4 hours at 45° C. The chromatographic system used was Alliance™ 2695 separation module from Waters Corporation (Milford, Mass.) coupled with three on-line detectors: a differential refractometer 2410 from Waters, a multi-angle light-scattering photometer Heleos™ 8+ from Wyatt Technologies (Santa Barbara, Calif.), and a differential capillary viscometer ViscoStar™ from Wyatt Technologies. The columns used for SEC were two Shodex (Showa Denko America, New York) GPC HFIP-806M™ styrene-divinyl benzene columns and one Shodex GPC HFIP-804M™ styrene-divinyl benzene column. The mobile phase was redistilled HFIP with 0.01 M sodium trifluoroacetate. Chromatographic conditions used were 50° C. at column and detector compartments, 40° C. at sample and injector compartments, a flow rate of 0.5 mL/min, and injection volume of 100 μL. Software packages used for data reduction were Astra version 6 from Wyatt (triple detection method with column calibration).

Example 1

Preparation of Acid-Exchanged Poly Alpha-1,3-Glucan

This Example describes producing acid-exchanged poly alpha-1,3-glucan, which can be used for preparing ester derivatives of poly alpha-1,3-glucan.

Acid-exchanged poly alpha-1,3-glucan was prepared by placing 10 g of poly alpha-1,3-glucan in a 250-mL glass beaker with 150 mL of DI water. This mixture was boiled for one hour on a hot plate, afterwhich the poly alpha-1,3-glucan was recovered by vacuum filtration. The poly alpha-1,3-glucan was then subjected to two acid exchange steps of stirring it with 100 mL of glacial acetic acid at room temperature followed by vacuum filtration, thereby providing acid-exchanged poly alpha-1,3-glucan.

Other forms of acid-exchanged poly alpha-1,3-glucan were also prepared by following the above process, but using propionic acid or butyric acid instead of acetic acid.

Acid-exchanged poly alpha-1,3-glucan prepared by these techniques was used in certain of the following examples to prepare various poly alpha-1,3-glucan ester derivatives. Since the acid exchange process removes water from the poly alpha-1,3-glucan, introduction of acid-exchanged poly alpha-1,3-glucan to an esterification reaction with an acid anhydride does not introduce water which may react with the acid anhydride.

Example 2

Preparation of Poly Alpha-1,3-Glucan Acetate

This Example describes producing the glucan ester derivative, poly alpha-1,3-glucan acetate.

Acid-exchanged poly alpha-1,3-glucan (10 g) as prepared in Example 1 using acetic acid was added to a mixture containing 180 mL of acetic acid and 1.84 g of sulfuric acid in a 500-mL round bottom flask equipped with a magnetic stir bar, thermocouple and condenser. This mixture was stirred for 1 minute at ambient temperature, afterwhich acetic anhydride (50 mL) was added to the mixture. The reaction was allowed to proceed for 30 minutes at ambient temperature, and then heated in a water bath at 35° C. for 20 minutes followed by heating to 50° C. for 30 minutes. The resulting reaction preparation did not contain any solids. The reaction was then removed from the water bath and allowed to chill for 15 minutes to reach 42° C. The reaction was then quenched with 25 mL of 70% acetic acid and stirred for 40 minutes. Poly alpha-1,3-glucan acetate was precipitated using an air-powered blender and DI water. The solid was washed twice with water for 30 minutes, followed by one wash with 5% sodium bicarbonate. The poly alpha-1,3-glucan acetate solid was then finally washed with water until neutral pH was achieved (two water washes). The solid was collected by vacuum filtration, dried under vacuum, and characterized by NMR and SEC. This method yielded poly alpha-1,3-glucan acetate with a DoS of 2.3 and an $M_n$ of 29170.

Thus, the ester derivative, poly alpha-1,3-glucan acetate, was prepared and isolated.

Example 3

Additional Preparation of Poly Alpha-1,3-Glucan Acetate

This Example describes producing the glucan ester derivative, poly alpha-1,3-glucan acetate, using various reaction conditions.

Acid-exchanged poly alpha-1,3-glucan was prepared as in Example 1 using acetic acid. A mixture of 180 mL acetic acid and 0.08 g of concentrated sulfuric acid was prepared in a 500-mL round bottom flask equipped with a magnetic stir bar and thermocouple; this mixture was chilled to 18° C. The acid-exchanged poly alpha-1,3-glucan (10 g) was slowly added to the chilled mixture and stirred for 1 minute. Acetic anhydride (50 mL) was then added to the mixture. The reaction was allowed to proceed for 10 minutes with no heating, and then heated in a water bath at 35° C. for 20 minutes. The resulting reaction, which was devoid of any solid, was chilled to 22° C. over 7 minutes using an ice bath. The reaction was then quenched with 25 mL of 70% acetic acid and stirred for 40 minutes. Poly alpha-1,3-glucan acetate was precipitated, washed and analyzed as described in Example 2. This process yielded poly alpha-1,3-glucan acetate with a DoS of 2.41 and an $M_n$ of 73960.

Using different concentrations of reagents allowed for different ester products to be formed. Table 1 below shows different poly alpha-1,3-glucan acetate esters synthesized using processes similar to the above process, but with certain modifications as indicated in the table. The results in Table 1 indicate that by altering the reaction conditions and the molecular weight of poly alpha-1,3-glucan starting material used in the reaction, the DoS by acetyl groups in the ester product, as well as the molecular weight of the product, can be altered.

TABLE 1

Poly Alpha-1,3-Glucan Acetate Prepared from Poly Alpha-1,3-Glucan

| Poly alpha-1,3-glucan starting material | | Reaction time and temp[a]. | | Amount of acetic anhydride and sulfuric acid catalyst used in each reaction | | Poly alpha-1,3-glucan acetate product | |
|---|---|---|---|---|---|---|---|
| | Amount | | | Acetic anhydride | Sulfuric Acid | | |
| $M_n$ | (g) | ° C. | min | (mL) | (%) | $M_n$ | DoS |
| 66K | 10 | 36 | 40 | 50 | 0.9 | 73960 | 2.41 |
| 66K | 10 | 30 | 45 | 50 | 1.6 | 78160 | 2.55 |
| 78K | 50 | 47 | 35 | 84 | 1.8 | 58800 | 2.57 |
| 66K | 10 | 36 | 30 | 50 | 0.8 | 48940 | 2.15 |
| 66K | 10 | 32 | 45 | 50 | 0.8 | 87510 | 2.6 |

[a]Temperature after heating the reaction.

Thus, various forms of the ester derivative, poly alpha-1,3-glucan acetate, were prepared and isolated.

Example 4

Additional Preparation of Poly Alpha-1,3-Glucan Acetate

This Example describes a process having a hydrolysis step for producing poly alpha-1,3-glucan acetate.

Acid-exchanged poly alpha-1,3-glucan (28 g) as prepared in Example 1 using acetic acid was added to a mixture containing 93.4 mL of acetic acid and 2.24 g of concentrated sulfuric acid and mixed. This mixture was added to a 1-L jacketed reaction vessel equipped with an overhead stirrer and thermocouple, and chilled to 12° C. using a recirculating bath. The reaction mixture was then stirred for 1 minute before acetic anhydride (89 mL) was added. The reaction was heated using a recirculation bath set at 42° C. for 40 minutes. The reaction at this stage, which was devoid of any solid, was quenched with 15.25 g (24%) magnesium acetate with excess water to reduce sulfuric acid content to 2%. The reaction was then heated to 100° C. over 25 minutes, afterwhich it was stirred at this temperature for 2 hour. The reaction was completely quenched by adding 24% magnesium acetate in 5% excess (6.1 g). Poly alpha-1,3-glucan acetate was precipitated, washed and analyzed as in Example 2. This process yielded poly alpha-1,3-glucan acetate with a DoS of 2.58.

Thus, the ester derivative, poly alpha-1,3-glucan acetate, was prepared using a method incorporating a hydrolysis step.

Example 5

Preparation of Poly Alpha-1,3-Glucan Acetate Via Hydrolysis of Poly Alpha-1,3-Glucan Triacetate This Example describes, in part, preparing poly alpha-1,3-glucan acetate by hydrolysis of poly alpha-1,3-glucan triacetate.

Poly alpha-1,3-glucan triacetate was first prepared as follows.

Acetic acid (384 mL), acetic anhydride (990 mL), and methylene chloride (890 mL) were mixed. This preparation was added to a 4-L glass reaction vessel equipped with an overhead stirrer and thermocouple, and chilled to 12° C. Acid-exchanged poly alpha-1,3-glucan (130 g) as prepared in Example 1 using acetic acid was slowly added to the chilled mixture and stirred for 1 minute. Perchloric acid (0.1 N) in acetic acid (180 mL) was then added. The reaction was allowed to proceed at ambient temperature for 3 hour and 35 minutes. The reaction, which was devoid of any solids, was then added to an air-powered blender containing methanol to precipitate poly alpha-1,3-glucan triacetate. The poly alpha-1,3-glucan triacetate solid thus formed was washed for 30 minutes with methanol followed by two washes with deionized (DI) water and one wash with 5% sodium bicarbonate. The poly alpha-1,3-glucan triacetate solid was then finally washed with water until neutral pH was achieved (two water washes) and collected by vacuum filtration, dried under vacuum, and characterized by NMR and SEC. The poly alpha-1,3-glucan triacetate produced had a DoS of 3.0 and an $M_n$ of 132300.

The poly alpha-1,3-glucan triacetate produced above was set up for hydrolysis by first dissolving it in 80 mL of acetic acid. DI water (4 mL) was then added to this preparation and stirred using a magnetic stir bar until thoroughly mixed. The preparation was then transferred to a Parr Reactor (Parr Instrument Company, Moline, Ill.); steam at a pressure of 5 $kg/cm^2$ was blown into the reactor to raise the temperature to 150° C. in 12 minutes. The preparation was held at this temperature for 50 minutes. The pressure was then increased from 5 $kg/cm^2$ to 8.37 $kg/cm^2$, afterwhich the reaction vessel was chilled to ambient temperature. The preparation retrieved from the reactor was yellow in color. However, upon addition of DI water, white solids of poly alpha-1,3-glucan acetate precipitated. This poly alpha-1,3-glucan acetate was isolated using vacuum filtration, and washed and analyzed as in Example 2. This process yielded poly alpha-1,3-glucan acetate with a DoS of 2.4 and an $M_n$ of 44200.

Thus, poly alpha-1,3-glucan acetate with a DoS below 2.75 was prepared from poly alpha-1,3-glucan triacetate.

Example 6

Preparation of Poly Alpha-1,3-Glucan Propionate

This Example describes producing the glucan ester derivative, poly alpha-1,3-glucan propionate.

Acid-exchanged poly alpha-1,3-glucan ($M_n$ of 119130) was prepared as described in Example 1 except that propionic acid was used instead of acetic acid. Propionic acid (8 mL) and sulfuric acid (0.03 g) were mixed in a 250-mL round bottom flask and chilled to 18° C. The acid-exchanged poly alpha-1,3-glucan (2 g) was slowly added to the chilled mixture and stirred for 1 minute. Propionic anhydride (10 mL) was then added to this preparation, afterwhich 0.6 mL glacial acetic acid was added. The reaction was allowed to proceed for 5 minutes with no heating, and then heated in a water bath at 42° C. for 1 hour and 45 minutes. The maximum temperature was not allowed to go beyond 43° C. to avoid excess degradation of molecular weight. The resulting reaction preparation, which was devoid of any solids, was chilled to 20° C. using an ice bath over 5 minutes. The reaction was then quenched with 4 mL of 50% aqueous acetic acid and stirred for 45 minutes. Poly alpha-1,3-glucan propionate was precipitated using an air-powered blender and DI water. The solid was washed twice with water for 30 minutes followed by a wash with 5% sodium bicarbonate. The poly alpha-1,3-glucan propionate solid was then washed with water until neutral pH was achieved (two water washes). The solid was collected by vacuum filtration, dried under vacuum, and characterized by NMR and SEC. The solid was confirmed as poly alpha-1,3-glucan propionate with 44.1 wt % propionyl groups (0 wt % acetyl groups) and an $M_n$ of 59510.

Thus, the ester derivative, poly alpha-1,3-glucan propionate, was prepared and isolated.

Example 7

Preparation of Poly Alpha-1,3-Glucan Acetate Butyrate

This Example describes producing the glucan mixed ester derivative, poly alpha-1,3-glucan acetate butyrate.

Acid-exchanged poly alpha-1,3-glucan (10 g) as prepared in Example 1 with acetic acid was added to a mixture containing 21 mL of glacial acetic acid, 20 mL of butyric acid and 0.09 g of sulfuric acid in a 500-mL round bottom flask equipped with a magnetic stir bar, thermocouple and condenser. The mixture was chilled to 18° C. using an ice bath and stirred for 1 minute before butyric anhydride (39 mL) was added to the flask. The reaction was allowed to proceed for 10 minutes with no heating, and then heated in a water bath at 35° C. for 80 minutes, followed by heating to 39° C. for 30 minutes where the maximum temperature reached was 39° C. to avoid excess degradation of product molecular weight. The resulting viscous solution, which was devoid of any solids, was cooled to 20° C. using an ice bath for 10 minutes. The reaction was then quenched with 20 mL of 50% aqueous acetic acid and stirred for 40 minutes. Solid poly alpha-1,3-glucan acetate butyrate was precipitated using an air-powered blender and DI water. The solid was washed twice with water for 30 minutes, followed by washing with 5% sodium bicarbonate. The solid thus obtained was then finally washed with DI water until neutral pH was achieved (two water washes). The solid was collected by vacuum filtration, dried under vacuum, and characterized by NMR and SEC. This process yielded poly alpha-1,3-glucan acetate butyrate mixed ester with a butyryl DoS of 1.0, an acetyl DoS of 1.3, and a number-average molecular weight ($M_e$) of 66340.

Using different concentrations of reagents allowed for different mixed ester products to be formed. Table 2 below shows different poly alpha-1,3-glucan acetate butyrate esters synthesized using processes similar to the above process, but with certain modifications as indicated in the table. The results in Table 2 indicate that by altering the reaction conditions and the molecular weight of poly alpha-1,3-glucan starting material used in the reaction, the amount of acetyl and butyryl groups in the mixed ester product, as well as the molecular weight of the product, can be altered.

TABLE 2

Poly Alpha-1,3-Glucan Acetate Butyrate Prepared from Poly Alpha-1,3-Glucan

| Poly alpha-1,3-glucan starting material | | | Amount of acetic acid, butyric acid, butyric anhydride, acetic anhydride and sulfuric acid used in each reaction | | | | | Reaction time and temp[b]. | | Poly alpha-1,3-glucan acetate butyrate product | | |
|---|---|---|---|---|---|---|---|---|---|---|---|---|
| | Amount | Acid | Acetic acid | Butyric Acid | Butyric Anhydride | Acetic Anhydride | Sulfuric Acid | | | | wt % | wt % |
| $M_n$ | (g) | exchange[a] | (mL) | (mL) | (mL) | (mL) | (g) | min | ° C. | $M_n$ | acetyl | butyryl |
| 62714 | 10 | acetic | 5 | 35 | 50 | 0 | 0.09 | 100 | 36 | 58680 | 12.8 | 32.6 |
| 47009 | 2 | butyric | 1 | 8 | 10 | 0 | 0.03 | 97 | 48 | 67700 | 1.8 | 42.7 |
| 47009 | 2 | butyric | 1 | 8 | 10 | 0 | 0.03 | 70 | 50 | 29777 | 2.7 | 37.8 |
| 119130 | 2 | acetic | 4 | 4 | 3 | 7 | 0.02 | 54 | 40 | 145300 | 34.7 | 9.4 |

[a]Acid exchange performed following procedure of Example using either acetic acid or butyric acid.
[b]Temperature after heating the reaction.

Thus, various forms of the mixed ester derivative, poly alpha-1,3-glucan acetate butyrate, were prepared and isolated.

Example 8

Preparation of Poly Alpha-1,3-Glucan Acetate Propionate

This Example describes producing the glucan mixed ester derivative, poly alpha-1,3-glucan acetate propionate.

Acid-exchanged poly alpha-1,3-glucan was prepared as described in Example 1 using acetic acid. A mixture of 35 mL of propionic acid and 0.09 g sulfuric acid was prepared in a 500-mL round bottom flask and chilled to 18° C. Acid-exchanged poly alpha-1,3-glucan solid (10 g) was slowly added to the chilled mixture and stirred for 1 minute. Propionic anhydride (50 mL) was then added, afterwhich 5 mL of glacial acetic acid was added. The reaction was allowed to proceed for 10 minutes with no heating, and then heated in a water bath at 30° C. for 1 hour, followed by heating to 34° C. for 10 minutes. The maximum temperature was not allowed to go beyond 36° C. to avoid excess degradation of product molecular weight. The solution thus obtained, which was devoid of any solids, was chilled to 20° C. in an ice bath for 5 minutes. The reaction was then quenched with 20 mL of 50% aqueous acetic acid and stirred for 40 minutes. Poly alpha-1,3-glucan acetate propionate was precipitated from the solution using an air-powered blender and DI water. The solid poly alpha-1,3-glucan acetate propionate product was washed twice with water for 30 minutes followed by a wash with 5% sodium bicarbonate. The solid was then washed with water until neutral pH was achieved (two water washes). The solid was collected by vacuum filtration, dried under vacuum, and characterized by NMR and SEC. The solid created was confirmed as a poly alpha-1,3-glucan acetate propionate containing 17.6 wt % acetyl and 32.9 wt % propionyl groups and having an $M_n$ of 64030.

Using different concentrations of reagents allowed for different mixed ester products to be formed. Table 3 below shows different poly alpha-1,3-glucan acetate propionate esters synthesized using processes similar to the above process, but with certain modifications as indicated in the table. The results in Table 3 indicate that by altering the reaction conditions and the molecular weight of poly alpha-1,3-glucan starting material used in the reaction, the amount of acetyl and propionyl groups in the mixed ester product, as well as the molecular weight of the product, can be altered.

TABLE 3

Poly Alpha-1,3-Glucan Acetate Propionate Prepared from Poly Alpha-1,3-Glucan

| Poly alpha-1,3-glucan starting material | | | Amount of acetic acid, propionic acid, propionic anhydride and sulfuric acid used in each reaction | | | | Reaction time and temp[b]. | | Poly alpha-1,3-glucan acetate propionate product | | |
|---|---|---|---|---|---|---|---|---|---|---|---|
| | Amount | Acid | Acetic acid | Propionic Acid | Propionic Anhydride | Sulfuric Acid | | | | wt % | wt % |
| $M_n$ | (g) | exchange[a] | (mL) | (mL) | (mL) | (g) | min | ° C. | $M_n$ | acetyl | propionyl |
| 62714 | 10 | propionic | 3 | 29 | 55 | 0.08 | 135 | 38 | 54460 | 7.4 | 35.9 |
| 62714 | 10 | propionic | 5 | 35 | 50 | 0.09 | 135 | 38 | 53450 | 4.9 | 41.1 |
| 71127 | 10 | propionic | 3 | 35 | 50 | 0.15 | 75 | 53 | 66190 | 1.7 | 47.1 |
| 47009 | 2 | propionic | 1 | 8 | 9 | 0.03 | 60 | 40 | 61640 | 6.5 | 41.6 |
| 25587 | 1 | propionic | 0.3 | 3.5 | 5 | 0.009 | 56 | 43 | 21380 | 1.4 | 49.0 |
| 119130 | 2 | propionic | 0.6 | 8 | 10 | 0.03 | 55 | 45 | 59150 | 0 | 44.1 |

[a]Acid exchange performed following procedure of Example using propionic acid instead of acetic acid.
[b]Temperature after heating the reaction.

Thus, various forms of the mixed ester derivative, poly alpha-1,3-glucan acetate propionate, were prepared and isolated.

Example 9

Preparation of Poly Alpha-1,3-Glucan Triacetate Using Sulfuric Acid as Catalyst

This Example describes producing poly alpha-1,3-glucan triacetate using sulfuric acid as the catalyst in the reaction.

Acid-exchanged poly alpha-1,3-glucan was prepared as described in Example 1 using acetic acid. A mixture of 180 mL acetic acid and 1.84 g of concentrated sulfuric acid, as a catalyst, was prepared in a 500-mL round bottom flask equipped with an overhead stirrer and thermocouple. Acid-exchanged poly alpha-1,3-glucan (10 g) was slowly added to the mixture and stirred under nitrogen for 1 minute. This mixture was chilled to about 18° C. using an ice bath. Acetic anhydride (50 mL) was added to the reaction, which was then heated to 80° C. over 45 minutes and allowed to react at this temperature for 30 minutes. The reaction, which was devoid of any solids, was chilled to 40° C. using an ice bath over 5 minutes. The reaction was then quenched with 25 mL of 70% acetic acid and stirred for 30 minutes. Poly alpha-1,3-glucan triacetate was precipitated using an air-powered blender (Waring, Torrington, Conn.) and DI water. The solid poly alpha-1,3-glucan triacetate product was washed with water for 30 minutes twice, followed by washing with 5% sodium bicarbonate. The solid was then washed with water until neutral pH was achieved (two water washes). The solid was collected by vacuum filtration, dried under vacuum, and characterized by NMR and SEC. This process yielded 7.8 g of poly alpha-1,3-glucan triacetate with a DoS of 3.1 and an $M_n$ of 5130. The DoS reading over 3.0 likely reflects integration variability typical to the NMR measurement process.

Table 4 below shows different molecular weight poly alpha-1,3-glucan triacetate esters synthesized using processes similar to the above process, but with certain modifications as indicated in the table. The results in Table 4 indicate that by altering the reaction conditions and the molecular weight of poly alpha-1,3-glucan starting material used in the reaction, the molecular weight of the product can be altered.

TABLE 4

Poly Alpha-1,3-Glucan Triacetate Esters Prepared from Poly Alpha-1,3-Glucan Using Sulfuric Acid Catalyst

| Poly alpha-1,3-glucan starting material | | Reaction time and temp[a]. | | Sulfuric Acid (wt % of glucan) | Poly alpha-1,3-glucan triacetate product | |
|---|---|---|---|---|---|---|
| $M_n$ | Amount (g) | ° C. | min | | $M_n$ | DoS |
| 112K | 10 | 43 | 40 | 8 | 68090 | 2.75 |
| 66K | 10 | 59 | 60 | 8 | 29380 | 2.94 |
| 66K | 28 | 39 | 55 | 8 | n/a | 2.91 |

[a]Maximum temperature after heating the reaction.

Thus, various forms of poly alpha-1,3-glucan triacetate were prepared and isolated in reactions using sulfuric acid as a catalyst.

Example 10

Preparation of Poly Alpha-1,3-Glucan Triacetate Using Perchloric Acid as Catalyst This Example describes producing poly alpha-1,3-glucan triacetate using perchloric acid as the catalyst in the reaction.

Acid-exchanged poly alpha-1,3-glucan was prepared as described in Example 1 using acetic acid. A mixture of 384 mL acetic acid, 990 mL acetic anhydride, and 890 mL methylene chloride was prepared in a 4-L glass reaction vessel equipped with an overhead stirrer and thermocouple, and chilled to 12° C. Acid-exchanged poly alpha-1,3-glucan (130 g) was slowly added to the chilled mixture and stirred for 1 minute. Perchloric acid (0.1 N) in acetic acid (180 mL) was then added to the mixture. The reaction was allowed to proceed at ambient temperature for 3 hour and 35 minutes. The resulting reaction, which was devoid of solid, was added to an air-powered blender containing methanol to precipitate poly alpha-1,3-glucan triacetate. The poly alpha-1,3-glucan triacetate solid was washed for 30 minutes with methanol followed by washing twice with DI water and one wash with 5% sodium bicarbonate. The poly alpha-1,3-glucan triacetate was then washed with water until neutral pH was achieved (two water washes). The solid was collected by vacuum filtration, dried under vacuum, and characterized by NMR and SEC. This process produced 221.5 g of poly alpha-1,3-glucan triacetate with a DoS of 3.2 and an $M_n$ of 132300. The DoS reading over 3.0 likely reflects integration variability typical to the NMR measurement process.

Table 5 below shows different molecular weight poly alpha-1,3-glucan triacetate esters synthesized using processes similar to the above process, but with certain modifications as indicated in the table. The results in Table 5 indicate that by altering the reaction conditions and the molecular weight of poly alpha-1,3-glucan starting material used in the reaction, the molecular weight of the product can be altered.

TABLE 5

Poly Alpha-1,3-Glucan Triacetate Esters Prepared from Poly Alpha-1,3-Glucan Using Perchloric Acid Catalyst

| Poly alpha-1,3-glucan starting material | | Reaction time and temp[a]. | | | Poly alpha-1,3-glucan triacetate product | |
|---|---|---|---|---|---|---|
| $M_n$ | Amount (g) | ° C. | min | Perchloric Acid (g) | $M_n$ | DOS |
| 126K | 130 | 32 | 180 | 1.80 | 132300 | 3.0 |
| 82K | 30 | 30 | 270 | 0.49 | 130700 | 3.0 |
| 66K | 130 | 41 | 150 | 2.17 | 93510 | 2.75 |
| 98K | 130 | 37 | 215 | 1.80 | 197000 | 3.0 |

[a]Maximum temperature after heating the reaction.

Thus, various forms of poly alpha-1,3-glucan triacetate were prepared and isolated in reactions using perchloric acid as a catalyst.

Example 11

Preparation of Films Using Poly Alpha-1,3-Glucan Acetate

Poly alpha-1,3-glucan acetate, prepared as in Example 2, was dissolved in acetone at 10 wt % mixture to make a solution. The solution was then cast onto a clean glass plate with a film caster and the solvent was allowed to evaporate to dryness to provide a film. The film was removed from the glass and rinsed with DI water. Table 6 shows properties of two different poly alpha-1,3-glucan acetate films prepared using two different samples of poly alpha-1,3-glucan acetate.

TABLE 6

Poly Alpha-1,3-Glucan Acetate Films

| Poly alpha-1,3-glucan acetate DoS | Poly alpha-1,3-glucan acetate $M_n$ | Tensile ($kg/mm^2$) | Tear (gf/mil) | Tear (gf) | Average Thickness (microns) |
|---|---|---|---|---|---|
| 2.6 | 87510 | 208 | 2.4 | 5.6 | 58.4 |
| 2.74 | 57240 | 206 | 2.0 | 6.8 | 86.4 |

Example 12

Optical Analysis of Poly Alpha-1,3-Glucan Acetate Films

A sample of poly alpha-1,3-glucan acetate film, prepared as in Example 11, was analyzed for color and haze. The spectra that were collected were consistent with ASTM E1164-09a. Spectral Bandwidth (SBW)=1, at 1 nm interval and wavelength range=830-360 nm. Table 7 shows the results of this study.

TABLE 7

Optical Measurements of a Poly Alpha-1,3-Glucan Acetate Film

| Poly alpha-1,3-glucan acetate DoS | Poly alpha-1,3-glucan acetate $M_n$ | Haze | Transmittance |
|---|---|---|---|
| 2.6 | 78160 | 6.32% | 5.36% |

Example 13

Preparation of Poly Alpha-1,3-Glucan Triacetate Films

Poly alpha-1,3-glucan triacetate was prepared as described in Example 10. A 10 wt % solution of the poly alpha-1,3-glucan triacetate was prepared by dissolving 10 g of it in 90 g methylene chloride:methanol (11.5:1 v/v). This solution was then cast onto a clean glass plate with a Gardner Knife (Gardner Lab Inc., Bethesda, Md.). The solvent was allowed to evaporate to dryness. The film produced following solvent evaporation was removed from the glass and rinsed with DI water. Table 8 summarizes the tensile and tear data for poly alpha-1,3-glucan triacetate films produced using this method. It can be seen that variation of the $M_n$ and DoS of the constituent glucan ester results in providing different physical properties for the film produced.

TABLE 8

Poly Alpha-1,3-Glucan Triacetate Films

| Poly alpha-1,3-glucan triacetate DoS | Poly alpha-1,3-glucan triacetate $M_n$ | Tensile ($kg/mm^2$) | Tear/Thickness (gf/mil) | Tear (gf) | Average Thickness (micrometers) |
|---|---|---|---|---|---|
| 2.75 | 93510 | 139 | 1.4 | 6.9 | 129.5 |
| 3.0 | 93670 | 203 | 2.9 | 11.6 | 101.6 |
| 3.0 | 132300 | 154 | 2.5 | 14.8 | 152.4 |
| 3.0 | 197000 | 143 | 3.1 | 18.1 | 147.5 |

Example 14

Thermal Analysis of Poly Alpha-1,3-Glucan Triacetate Films

Poly alpha-1,3-glucan triacetate films as prepared in Example 13 were analyzed using MDSC and TGA. MDSC measurements were performed with 5-6 mg of film at a heating rate of 3° C./min, modulation amplitude of 0.48° C., and modulation period of 60 seconds starting from 0° C., in $N_2$ using Q1000 TA instrument.

TGA experiments were performed from ambient temperature to 800° C. under $N_2$ using Q500 TA instrument.

The information provided in Table 9 shows the heat stability/thermal degradation of the poly alpha-1,3-glucan triacetate films prepared according to the method disclosed above. Table 9 summarizes data acquired from the MDSC and TGA measurements. It can be seen that variation of the $M_n$ and DoS of the constituent glucan ester results in providing different physical properties for the film produced.

TABLE 9

MDSC and TGA Data for Poly Alpha-1,3-Glucan Triacetate Films

| Poly alpha-1,3-glucan triacetate (DoS/$M_n$) | Tg (° C.) (Reverse) | Tm (° C.), ΔH (J/g) Total Heat flow | Tm (° C.), ΔH (J/g) Non-Rev Heat flow | Onset of Decomposition (° C.) |
|---|---|---|---|---|
| 2.75/93510 | 188.0 | 333.0<br>29.6 | 332.9<br>16.8 | 349.3 |
| 3.0/197000 | 189.1 | 340.5<br>39.4 | 339.9<br>29.6 | 356.7 |

Example 15

Optical Analysis of Poly Alpha-1,3-Glucan Triacetate Films

Poly alpha-1,3-glucan triacetate films prepared as in Example 13 were analyzed for color and haze. Spectra were collected consistent with ASTM E1164-09a using spectral Bandwidth (SBW) of 1, at 1 nm interval and wavelength range of 830-360 nm. Results of optical measurements of poly alpha-1,3-glucan triacetate films are shown in Table 10.

TABLE 10

Optical Measurements of Poly Alpha-1,3-Glucan Triacetate Films

| Poly alpha-1,3-glucan triacetate DoS | Poly alpha-1,3-glucan triacetate $M_n$ | Haze (%) | Transmittance (%) |
|---|---|---|---|
| 3.0 | 130700 | 6.32 | 91.6 |
| 2.75 | 93510 | 1.41 | 92.1 |
| 2.72 | 53690 | 1.37 | 92.3 |

What is claimed is:

1. A composition comprising a poly alpha-1,3-glucan ester compound represented by the structure:

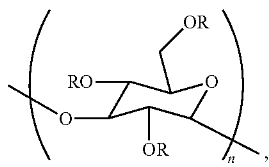

wherein
(i) n is at least 6,
(ii) each R is independently an H or acyl group, and
(iii) the compound has a degree of substitution by the acyl group of less than 2.75.

2. The composition of claim 1, wherein at least one acyl group is selected from the group consisting of acetyl, propionyl, butyryl, pentanoyl, hexanoyl, heptanoyl, and octanoyl.

3. The composition of claim 1, wherein the compound contains one type of acyl group.

4. The composition of claim 1, wherein the compound contains two or more types of acyl group.

5. The composition of claim 4, wherein the two or more types of acyl group are:
(i) acetyl and propionyl, or
(ii) acetyl and butyryl.

6. The composition of claim 1, wherein the compound has a degree of substitution by the acyl group of about 0.05 to about 2.70.

7. The composition of claim 6, wherein at least one acyl group is selected from the group consisting acetyl, propionyl, butyryl, pentanoyl, hexanoyl, heptanoyl, and octanoyl.

8. The composition of claim 6, wherein the compound contains one type of acyl group.

9. The composition of claim 8, wherein the acyl group is an acetyl group.

10. The composition of claim 9, wherein the compound has a degree of substitution by the acetyl group of about 0.05 to about 2.60.

11. The composition of claim 6, wherein the compound contains two or more types of acyl group.

12. The composition of claim 11, wherein the two or more types of acyl group are:

(i) acetyl and propionyl, or
(ii) acetyl and butyryl.

13. A method of producing a poly alpha-1,3-glucan ester compound, the method comprising:
(a) contacting poly alpha-1,3-glucan in a reaction that is substantially anhydrous with at least one acid catalyst, at least one acid anhydride, and at least one organic acid, wherein at least one acyl group is esterified to the poly alpha-1,3-glucan thereby producing a poly alpha-1,3-glucan ester compound represented by the structure:

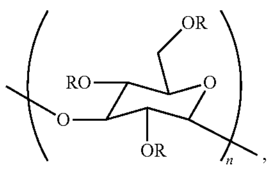

wherein
(i) n is at least 6,
(ii) each R is independently an H or acyl group, and
(iii) the compound has a degree of substitution by the acyl group of less than 2.75; and
(b) optionally, isolating the poly alpha-1,3-glucan ester compound produced in step (a).

14. The method of claim 13, wherein the compound has a degree of substitution by the acyl group of about 0.05 to about 2.70.

15. The method of claim 13, wherein the acid catalyst comprises sulfuric acid.

16. The method of claim 13, wherein:
the acid anhydride is one or more of acetic anhydride, propionic anhydride, or butyric anhydride; and
the organic acid is one or more of acetic acid, propionic acid, or butyric acid.

17. The method of claim 13, wherein the poly alpha-1,3-glucan is further contacted with an organic solvent in step (a).

18. The method of claim 13, wherein the compound contains one type of acyl group.

19. The method of claim 18, wherein the acyl group is an acetyl group.

20. The method of claim 13, wherein the percentage of glycosidic linkages of the poly alpha-1,3-glucan ester compound that are alpha-1,3 is at least 90%.

21. The method of claim 20, wherein the percentage of glycosidic linkages of the poly alpha-1,3-glucan ester compound that are alpha-1,3 is 100%.

22. The composition of claim 1, wherein the percentage of glycosidic linkages of the poly alpha-1,3-glucan ester compound that are alpha-1,3 is at least 90%.

23. The composition of claim 22, wherein the percentage of glycosidic linkages of the poly alpha-1,3-glucan ester compound that are alpha-1,3 is 100%.

24. The composition of claim 3, wherein the acyl group is an acetyl group.

* * * * *